Figure 1:
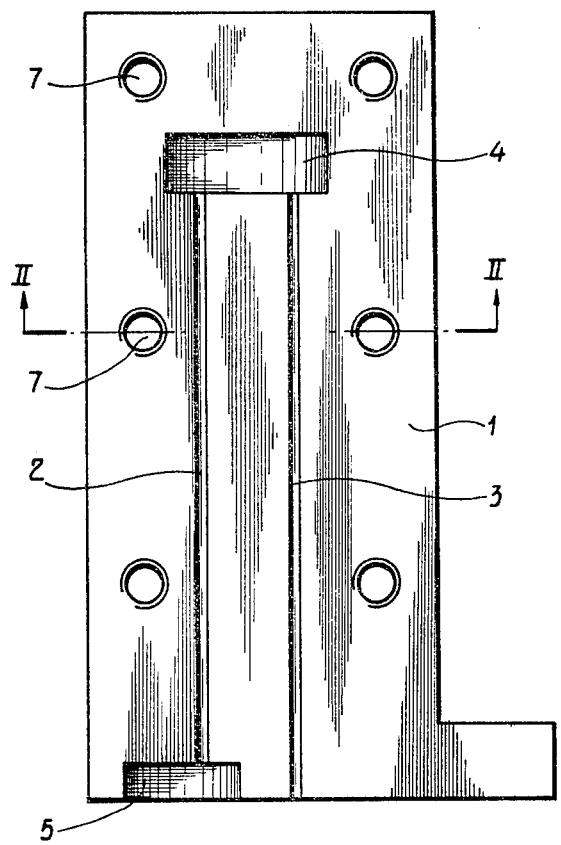

United States Patent [19]

van Breest Smallenburg

[11] Patent Number: 4,477,961
[45] Date of Patent: Oct. 23, 1984

[54] METHOD FOR MANUFACTURING A MEASURING CAPILLARY

[75] Inventor: Tjeerd van Breest Smallenburg, Krimpen a/d Ijssel, Netherlands

[73] Assignee: Tjeba Holding BV, Netherlands

[21] Appl. No.: 408,033

[22] Filed: Aug. 13, 1982

[30] Foreign Application Priority Data

Aug. 17, 1981 [NL] Netherlands ............... 8103839

[51] Int. Cl.³ .................. B23P 25/00; D03D 49/46
[52] U.S. Cl. ................................. 29/458; 138/141
[58] Field of Search ............... 29/458, 463, 157 R; 73/55, 56; 526/250; 138/39, 141

[56] References Cited

U.S. PATENT DOCUMENTS

| | | | |
|---|---|---|---|
| 3,342,063 | 9/1967 | Smythe | 73/55 |
| 3,734,139 | 5/1973 | Zafiroglu | 138/141 |
| 3,827,130 | 8/1974 | Baumann | 29/463 |
| 3,982,864 | 9/1976 | Cain | 29/458 |
| 4,113,407 | 9/1978 | Grzina | 29/463 |
| 4,156,127 | 5/1979 | Sako et al. | 138/141 |
| 4,241,602 | 12/1980 | Han | 73/56 |
| 4,304,038 | 12/1981 | Yabu et al. | 29/458 |
| 4,305,192 | 12/1981 | Becker | 29/463 |

FOREIGN PATENT DOCUMENTS 2343241  9/1977  France .

OTHER PUBLICATIONS

Leblanc, J. L., "New Slit Die Rheometer: Some Results With a Butadiene-Styrene Block Copolymer", *Polymer*, vol. 17, No. 3, pp. 235–240, Mar. 1976, Guildford (GB).

*Primary Examiner*—Howard N. Goldberg
*Assistant Examiner*—Steven E. Nichols
*Attorney, Agent, or Firm*—Berman, Aisenberg & Platt

[57] ABSTRACT

A method for manufacturing a measuring capillary, wherein in each of a number of substantially plate-shaped parts 1, a recess 2, 3 is formed. The shape of the recesses 2, 3 is such that when said plate-shaped parts 1 are superposed with the recesses 2,3 facing each other, said recesses 2,3 define the capillary. The walls of the recesses 2, 3 and at least the plate surface portions directly adjacent thereto are coated by a substance. The plate-shaped parts 1 are superposed such that the recesses 2, 3 formed therein together define a capillary and the plate-shaped parts 1 are secured to each other.

5 Claims, 2 Drawing Figures

METHOD FOR MANUFACTURING A MEASURING CAPILLARY

The invention relates to a method for maufacturing a measuring capillary. In particular the invention concerns a method for manufacturing a capillary for a viscosity meter for measuring and regulating the viscosity of heavy oils. This type of viscosity meter is mainly used in diesel engines.

For diesel engines it is extremely important that the viscosity of the fed fuel is as constant as possible so that the rate at which the fuel is atomized into the cylinders is also constant. For that purpose at least a portion of the fed fuel is passed through a measuring capillary, in which the measured pressure difference across said capillary is a measure for the viscosity of the fuel, which measuring result may be converted in a signal for heating the fuel more or less.

Until now such a measuring capillary has been obtained by drilling a channel having a circular cross-section and a diameter of approximately 1.5–1 mm into a block or plate of for example stainless steel, or by manufacturing a glass tube having an inner cross-section of said diameter.

However, the measuring capillaries obtained by said method have the disadvantage that, in using it in the viscosity meter for viscosity measurements of heavy oils, said measurements are made unreliable by deposits of oil residues onto the inner wall of the capillary.

The object of the invention is to provide a method for manufacturing a measuring capillary in which the obtained measuring capillary does not show said disadvantage.

Said object is achieved in that according to the method according to the invention in each of a number of substantially plate-shaped parts a recess is formed such that when said parts are superposed the recesses formed therein, define together a capillary, the walls of the recesses and at least the directly adjacent surface portions of the plate-shaped parts are provided with a coating of a certain substance, the plate-shaped parts are superposed such that the recesses formed therein define together a capillary and the plate-shaped parts are connected to each other.

In this way a measuring capillary is obtained of which the wall, in spite of the extremely small cross-section of the capillary, is coated with a substance preventing deposits from forming. By also coating the portions adjacent to the recesses of the various plate-shaped parts with said substance, sealings are obtained between the plate-shaped parts so that leakage is excluded.

Preferably the capillary is formed by superposing two plate-shaped parts in which a semicircular (in cross-section) recess is first formed in each.

Preferably the coating substance consists of polytetrafluoroethylene. Said substance prevents in an excellent way, deposits from building up, but may show the phenomenon of flow at room temperature. However, because in the method according to the invention the coating may be very thin, for example, in the order of 80 $\mu$m, said phenomenon has no influence on the stability of the dimension of the inner cross-section of the measuring capillary.

Figure 2:
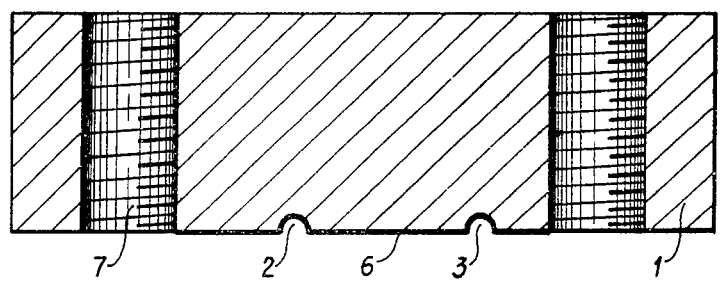

The invention will be described hereafter with reference to the drawing, in which FIG. 1 shows in top view of the plate-shaped parts for the manufacturing a measuring capillary according to the invention, FIG. 2 is an enlarged cross-section along the line II—II in FIG. 1.

As shown in the drawing in the top face of a plate-shaped part-1 two recesses 2 and 3 are formed. Adjacent to said semicircular recesses larger recesses 4 and 5 are formed.

The walls of the recesses 2 and 3 and the portions of the plate 1 adjacent to it, are subsequently coated with a layer of polytetrafluoroethylene 6 having has a thickness of, for example, 80 $\mu$m.

In similar way a second plate-shaped part is formed after which said second plate-shaped part is put in top of the first plate-shaped part such that the recesses 2 and 3 form together a continuous capillary having a circular cross-section. The plates are fixed to each other by means of bolts screwed into the threaded holes 7.

I claim:

1. A method for manufacturing a measuring capillary which comprises: forming, in each of a number of substantially plate-shaped parts, a recess having such a shape that, when said plate-shaped parts are superposed, the recesses formed therein together define a capillary; coating the walls of the recesses and surface portions of the plates directlly adjacent thereto with a substance; superposing the plate-shaped parts so that the recesses formed therein together define a capillary; and connecting the plate-shaped parts to each other.

2. A method according to claim 1, wherein the recesses are semicircular in cross-section and the substance is one which prevents deposits from forming.

3. A method according to claim 2, wherein the semicircular recesses have radii from about 0.5 mm to 0.75 mm.

4. A method according to one of claims 1 to 3 wherein said substance is polytetrafluoroethylene.

5. A method according to claim 4, wherein the substance is coated in a layer having a thickness of about 80 $\mu$m.

* * * * *